United States Patent
Hansen et al.

(10) Patent No.: US 10,772,649 B2
(45) Date of Patent: Sep. 15, 2020

(54) CLOT RETRIEVAL CATHETER

(71) Applicant: Cook Medical Technologies LLC, Bloomington, IN (US)

(72) Inventors: Palle Munk Hansen, Bjaeverskov (DK); Tue Thuren Bödewadt, Solroed Strand (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 280 days.

(21) Appl. No.: 15/717,305

(22) Filed: Sep. 27, 2017

(65) Prior Publication Data

US 2018/0064455 A1     Mar. 8, 2018

Related U.S. Application Data

(63) Continuation of application No. 14/842,268, filed on Sep. 1, 2015, now Pat. No. 9,801,643.

(60) Provisional application No. 62/044,512, filed on Sep. 2, 2014.

(51) Int. Cl.
    *A61B 17/221*     (2006.01)
    *A61B 17/00*      (2006.01)

(52) U.S. Cl.
    CPC .. *A61B 17/221* (2013.01); *A61B 2017/00867* (2013.01); *A61B 2017/2212* (2013.01)

(58) Field of Classification Search
    CPC ........ A61B 17/221; A61B 2017/00867; A61B 2017/2212
    See application file for complete search history.

(56) References Cited

U.S. PATENT DOCUMENTS

| | | | | |
|---|---|---|---|---|
| 5,897,567 A | * | 4/1999 | Ressemann | A61B 17/32 604/22 |
| 5,972,019 A | * | 10/1999 | Engelson | A61B 17/221 606/200 |
| 6,159,230 A | * | 12/2000 | Samuels | A61B 17/22031 606/200 |
| 6,165,200 A | * | 12/2000 | Tsugita | A61F 2/01 606/200 |
| 6,168,603 B1 | * | 1/2001 | Leslie | A61B 17/221 606/114 |
| 6,402,771 B1 | * | 6/2002 | Palmer | A61B 17/221 606/114 |

(Continued)

FOREIGN PATENT DOCUMENTS

WO    WO 2011/119872 A1    9/2011
WO    WO 2013/109756 A2    7/2013

*Primary Examiner* — Julie A Szpira
(74) *Attorney, Agent, or Firm* — Brinks Gilson & Lione

(57) ABSTRACT

A clot retrieval device, for example to be used in a thrombectomy, is provided including a catheter, an elongated member, and a knitted basket with a proximal end coupled to the catheter and a distal end coupled to the elongated member. The elongated member is movable between an expanded position and a compressed position relative to the catheter and is configured so that the knitted basket expands radially and compresses as the elongated member is moved to the compressed position. The knitted basket is comprised of a plurality of wires coupled together by a plurality of windings. Each winding comprises one of the plurality of the wires twisted about another of the plurality of wires.

17 Claims, 14 Drawing Sheets

(56) References Cited

U.S. PATENT DOCUMENTS

| | | | |
|---|---|---|---|
| 6,610,077 B1* | 8/2003 | Hancock | A61F 2/013 606/194 |
| 6,695,858 B1* | 2/2004 | Dubrul | A61B 17/221 606/159 |
| 7,285,126 B2* | 10/2007 | Sepetka | A61B 17/22031 606/113 |
| 7,374,564 B2* | 5/2008 | Brown | A61B 17/221 606/113 |
| 7,476,232 B2* | 1/2009 | Deal | A61M 25/04 606/127 |
| 8,088,140 B2* | 1/2012 | Ferrera | A61B 17/221 606/113 |
| 8,679,142 B2* | 3/2014 | Slee | A61F 2/90 606/159 |
| 9,278,201 B2* | 3/2016 | Rapaport | A61B 17/320725 |
| 10,064,635 B2* | 9/2018 | Martin | A61B 17/221 |
| 10,363,054 B2* | 7/2019 | Vale | A61F 2/013 |
| 10,426,510 B2* | 10/2019 | Farhangnia | A61B 17/32075 |
| 2001/0031980 A1* | 10/2001 | Wensel | A61B 17/221 606/200 |
| 2002/0058904 A1* | 5/2002 | Boock | A61B 17/22 604/35 |
| 2002/0123765 A1* | 9/2002 | Sepetka | A61B 17/22031 606/192 |
| 2003/0055445 A1* | 3/2003 | Evans | A61B 17/221 606/159 |
| 2003/0191492 A1* | 10/2003 | Gellman | A61B 17/221 606/200 |
| 2005/0043756 A1* | 2/2005 | Lavelle | A61B 17/221 606/200 |
| 2006/0155305 A1* | 7/2006 | Freudenthal | A61B 17/221 606/114 |
| 2006/0195137 A1* | 8/2006 | Sepetka | A61B 17/22 606/200 |
| 2007/0185501 A1* | 8/2007 | Martin | A61B 17/22012 606/114 |
| 2008/0091223 A1* | 4/2008 | Pokorney | A61B 17/221 606/159 |
| 2009/0069828 A1* | 3/2009 | Martin | A61B 17/221 606/159 |
| 2011/0172678 A1* | 7/2011 | Behl | A61M 25/0102 606/127 |
| 2011/0213403 A1* | 9/2011 | Aboytes | A61F 2/013 606/194 |

* cited by examiner

CLOT RETRIEVAL CATHETER

CROSS REFERENCE

This application is a continuation of and claims priority to U.S. patent application Ser. No. 14/842,268 filed on Sep. 1, 2015, which is hereby incorporated by reference. U.S. patent application Ser. No. 14/842,268 is a non-provisional application claiming priority to U.S. Provisional Patent Application No. 62/044,512 filed Sep. 2, 2014. Which is also hereby incorporated by reference.

BACKGROUND

The field of the present invention relates to devices to remove a thrombus from an intraluminal passage. Intravenous devices are commonly used during thrombectomies to remove a thrombus from blocking blood flow through an intraluminal passage. Frequently, an aspirator is brought to the blockage area to collect the thrombus by suction. However, aspirator catheters typically have a large cross-section and may be difficult to use in narrow intraluminal passages, particularly within the brain.

In such procedures, it is desirable to retrieve the thrombus or embolism and bring it to a wider area of the intraluminal passage for removal by an aspirator catheter. Several devices exist to accomplish this purpose, such as a wire within a catheter which deploys into a coil. However, these devices are difficult to maneuver to the desired intraluminal passage because of the tortuous angles within such area of vasculature and because the devices cannot be adequately steered to the site of the thrombus. Additionally, often the thrombus cannot be adequately contained within the device during retraction. If the thrombus fragments or escapes from the device during retraction, the thrombus or a portion of the thrombus may cause a blockage elsewhere in the vasculature causing significant harm to the patient.

It is desirable for a clot retrieval device to exist which has a small cross-sectional profile which can also be adequately steered to the clot within narrow intraluminal passages. Furthermore, it is desirable that such a device be capable of adequately capturing and containing the clot during retraction through the intraluminal passage.

SUMMARY

Further areas of applicability will become apparent from the description provided herein. It should be understood that the description and specific examples are intended for purposes of illustration only and are not intended to limit the scope of the present disclosure.

In one form of the present disclosure, a clot retrieval device is provided comprising an outer catheter comprising a distal end and a lumen through the distal end. The device further comprises an elongated member comprising an outer surface and a distal portion. The elongated member is configured to pass through the at least one lumen of the outer catheter and is movable relative to the outer catheter between an extended position and a compressed position. The device further comprises a knitted basket comprising a proximal end coupled to the distal portion of the elongated member. When the elongated member is in the extended position, the knitted basket is adjacent to the outer surface of the elongated member. When the elongated member is moved to the compressed position, at least a portion of the knitted basket expands radially from the outer surface of the elongated member. The knitted basket is comprised of a plurality of wires coupled together by a plurality of windings comprising one of the plurality of wires twisted about another of the plurality of wires.

In another form of the present disclosure, a clot retrieval device is provided comprising a catheter comprising a proximal end, a distal end, and a lumen through the distal end. The device further comprises an elongated member comprising an outer surface, a lumen, a proximal end, and a distal portion. The elongated member is configured to pass through the lumen of the catheter and is movable relative to the catheter between an extended position and a compressed position. The device further comprises a wire guide configured to pass through the lumen of the elongated member, and an expandable knitted basket comprising a proximal end coupled to the distal end of the catheter and a distal end coupled to the distal portion of the elongated member. The device further comprises an actuator comprising a first member coupled to the proximal end of the elongated member and a second member coupled to the proximal end of the elongated member. The actuator is configured to move the elongated member between the extended position and the compressed position.

BRIEF DESCRIPTION OF SEVERAL VIEWS OF THE DRAWINGS

The invention may be more fully understood by reading the following description in conjunction with the drawings, in which.

The drawings described herein are for illustration purposes only and are not intended to limit the scope of the present disclosure in any way.

DETAILED DESCRIPTION

Figure 1A:
FIGS. 1A-1C are side plan views of a clot retrieval device, showing an outer catheter, an inner elongated member and a knitted basket.
Figure 1B:
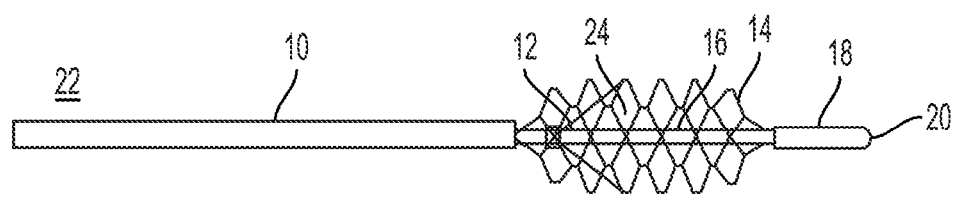
Figure 1C:
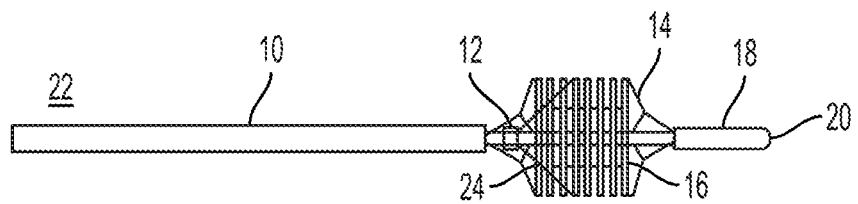

Referring now to the drawings, and particularly to FIGS. 1A-1C, a clot retrieval device 22 is shown comprising a catheter 10 having at least one lumen 38 through the distal end 34 (shown in FIG. 3), an elongated member 16 which is configured to pass through the lumen 38 of the catheter 10, and a knitted basket 14 having a proximal end coupled to the distal end 34 of the catheter 10 and a distal end coupled to the distal portion 18 of the elongated member 16.

The elongated member 16 is movable relative to the catheter 10 between a longitudinally extended position (shown in FIG. 1A) and a longitudinally compressed position (shown FIG. 1C). In the extended position, the distal portion 18 of the elongated member 16 is farthest from the distal end 34 of the catheter 10. In the compressed position, the distal portion 18 of the elongated member 16 is closest to the distal end 34 of the catheter 10. When the elongated member 16 is in the extended position relative to the catheter 10, the basket 14 is adjacent to or rests on the outer surface of the elongated member 16. As the elongated member 16 moves to the compressed position relative to the catheter 10, the basket 14 expands radially from the outer surface of the elongated member and compresses in length.

The distal portion 18 of the elongated member 16 may also include an atraumatic tip 20. This atraumatic tip may take the form of a simple rounded end, as shown in FIGS. 1A-1C or in the form of a flexible, floppy tip. The atraumatic tip 20 ensures that the device 22 may be used in a narrow intraluminal passage 28 without damaging the walls 26 of the intraluminal passage 28.

The elongated member 16 may also comprise a braid within the interior of the elongated member 16. The braid within the elongated member 16 may comprise Nitinol wire and extend the entire length of the elongated member 16 or may be included only in the portions of the elongated member 16 which are configured to extend beyond the catheter 10. The braid may extend into the distal portion 18 of the elongated member and may be connected to a portion of the wires 32 extending into the distal portion 18 by twisting, braiding, or welding.

The device 22 may also comprise a collar 12 coupled to the elongated member 16 so that, when the elongated member 16 is in the compressed position, the collar 12 is adjacent to or rests against the distal end 34 of the catheter 10. The collar 12 may be sized to be larger than the lumen 38 of the catheter 10 so that the collar 12 cannot be retracted into the catheter 10. When the collar 12 is moved against the distal end 34 of the catheter 10, the elongated member 16 may be prevented from being proximally moved beyond the compressed position. Alternatively, the collar 12 may take the form of any other projection which would prevent retraction into the lumen 38 of the catheter 10.

Additionally, the collar 12 may be used to monitor the positions of the elongated member 16 and the basket 14 using radioscopy. The device 22 may also comprise two radiopaque markers at the proximal and distal ends of the basket 14 to show the position of the basket within the intraluminal passage 28. The proximal marker may be coupled to the distal end 34 of the catheter 10 and the distal marker may be coupled to the distal portion 18 of the elongated member 16. When the elongated member 16 is moved towards the compressed position, the movement of the markers may be observed through radioscopy to indicate the position of the elongated member 16 relative to the catheter 10. If the collar 12 is also radiopaque, the operator may observe that the elongated member 16 is in the compressed position when the collar 12 is adjacent to the proximal marker.

Alternatively, a portion of the elongated member 16 may be comprised of a radiopaque material and used in conjunction with the markers to determine the positions of the elongated member 16 and the basket 14 using radioscopy. When the elongated member 16 is in the compressed position, and the basket 14 has been radially expanded, a portion of the elongated member 16 is exposed and outside of the catheter 10. This portion of the elongated member 16 may be made of a radiopaque material so that the operator may observe that the elongated member 16 is in the compressed position when the radiopaque portion of the elongated member 16 is adjacent to or overlapping with the proximal marker.

As another alternative, all or a portion of the wires 32 comprising the knitted basket 14 may be made from a radiopaque material, may have a radiopaque core, or may have a radiopaque coating applied to the wire 32. The radiopaque material may be platinum, gold, iridium, or any other alloy which is opaque to under radioscopy, such as DFT Wire manufactured by Fort Wayne Metals. A single wire 32 or a plurality of wires 32 in the knitted basket 14 which are radiopaque may ease the ability of an operator to position and operate the clot retrieval device 22 while using radioscopy.

The device 22 may also comprise at least one support wire 24 having a first end coupled to the elongated member 16 and a second end coupled to the basket 14. The first end is arranged proximally to the second end so that, as the basket 14 expands radially, the support wire 24 will contribute proximal force to the knitted basket 14, assisting in compressing the length of the basket 14 evenly as the basket 14 expands radially. More than one support wire 24 may be desired depending on the length of the basket 14.

Figure 2A:
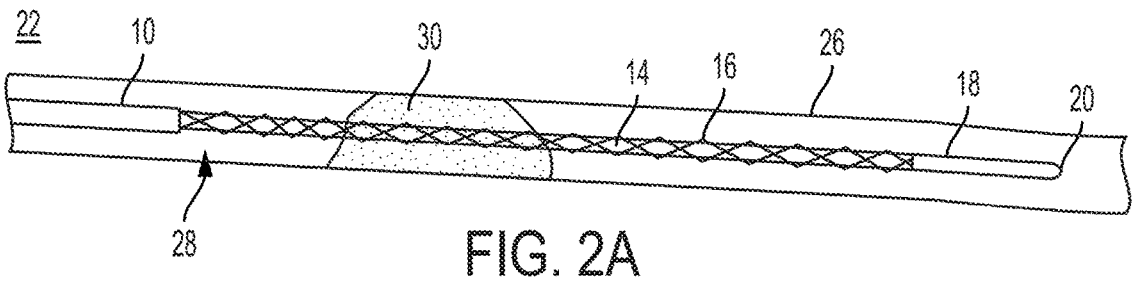
FIGS. 2A-2C are side plan views of a clot retrieval device, showing the device in an intraluminal passage alongside a thrombus.
Figure 2B:
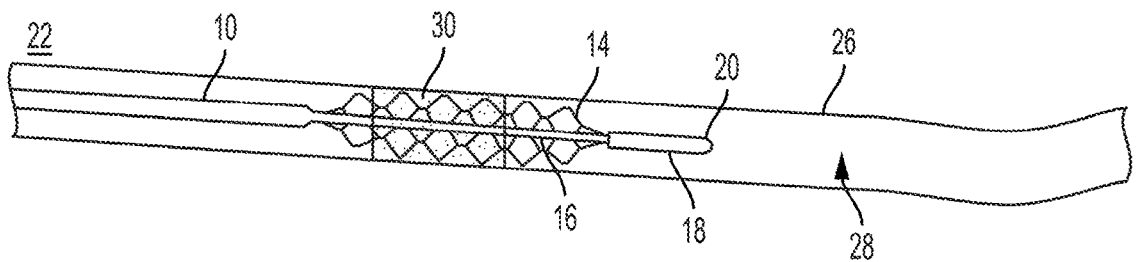
Figure 2C:
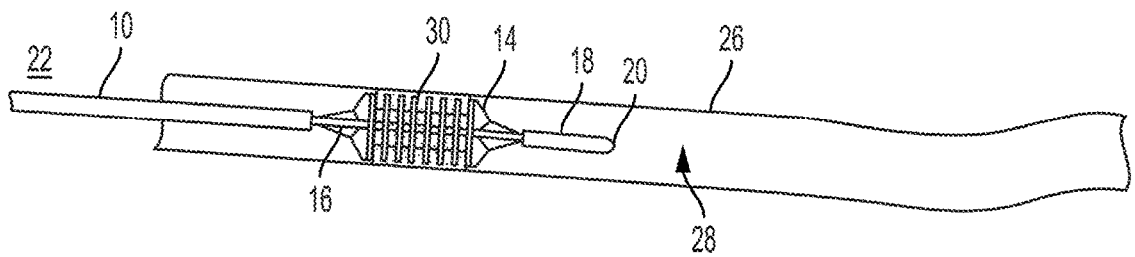

Referring to FIGS. 2A-2C, a possible embodiment of the clot retrieval device 22 is shown within an intraluminal passage 28. FIG. 2A shows the device 22 with the elongated member 16 in the extended position, with the knitted basket 14 adjacent to the outer surface of the elongated member 16. In this position, the device 22 can more easily be positioned within the intraluminal passage 28, and can pass through or around the thrombus 30 or blockage.

As shown in FIG. 2B, once the distal end of the elongated member has passed through or around the thrombus 30 so that the knitted basket 14 overlaps at least a portion of the thrombus 30, the inner elongated member 16 is moved to the compressed position. As the knitted basket 14 begins to expand radially in response to the movement of the elongated member 16, the wires 114 that comprise the knitted basket 14 pass through or around the thrombus 30 and may reach the walls 26 of the intraluminal passage 28.

As shown in FIG. 2C, once the elongated member 16 is in the compressed position and the knitted basket 14 has been fully expanded, the thrombus 30, or a portion of the thrombus 30, will be contained within the knitted basket 14. From this configuration, the clot retrieval device 22 may be retracted to remove the thrombus 30 from the intraluminal passage 28.

Figure 3:
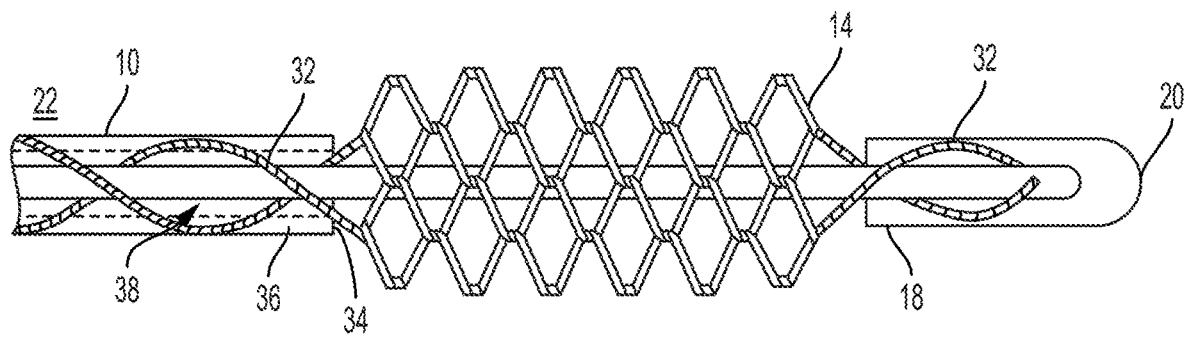
FIG. 3 is a partial cross-sectional view of a clot retrieval device, showing an outer catheter, an inner elongated member, and a knitted basket which transitions to a several pairs of helical wires.

Referring to FIG. 3, a partial cross-sectional view of the clot retrieval device 22 is shown. In this embodiment, the knitted basket 14 is comprised of a plurality of wires 114 which are embedded in both the catheter 10 and the distal portion 18 of the elongated member 16. Although it is not readily apparent from the illustration of FIG. 3 that the wires 32 are formed into helical wires 32 in a continuous braided twist within the catheter wall 36 and the distal portion 18 of the elongated member 16, it is preferable for the helical wires 32 to be braided or twisted together within these embedded portions. Furthermore, the wires 32 embedded in the catheter wall 36 spiral around the catheter 10 as shown in FIG. 3. Between the distal end 34 of the catheter 10 and the distal portion 18 of the elongated member 16, the wires 114 extend in a knitted pattern to form the knitted basket 14, although the knitting of the wires 114 may not be apparent from the embodiment shown in FIG. 3. Although the embodiment shown in FIG. 3 shows only two helical wires 32, the clot retrieval device 22 may have many helical wires 32 which separate to be integrated into the knitted basket 14. Alternatively, the wires 114 may be embedded within the catheter 10 without twisting, simply wrapping around within the walls 36 of the catheter 10 to the distal end 34 where the knitted basket 14 begins. The helical wires 32 are distinguished from the wires 114 in the knitted basket 14 in that the helical pairs 118 of wires 32 are continuously braided or twisted together so as to be adjacent to one another, never separating until transitioning to individual wires 114 to be incorporated into the knitted basket 14. Within the walls 36 of the catheter 10, it may be desirable for the wires 32 to extend the entire length of the catheter 10, from the proximal end to the distal end 34 of the catheter 10.

The wires 32 may have three stages of interaction depending upon their position along the catheter 10. Within the catheter 10, the wires 32 may be configured in a first stage comprising a braid, crossing over and under one another in as they circle about the catheter wall 36. The wires 32 in this first stage may have a flat cross-sectional shape to reduce their cross-sectional area. As the wires 32 extend from the distal end 34 of the catheter 10, but before the knitted basket 14, the wires 32 may be configured in a second stage comprising a continuous twist (Example in FIG. 5B, Reference Number 162). If the cross-sectional shape of the wire 32 changes between the first and second stage of the wires 32, the wires 32 may be welded together inside or outside the catheter 10. If the catheter 10 includes a radiopaque marker at the distal end 34 of the catheter 10, the wires may transition from the first stage configuration to the second stage configuration under the radiopaque marker. The wires 32 are also configured in a third stage comprising the knitted basket 14. The wires 32 may return to the second stage configuration and first stage configuration as the wires 32 extend distally beyond the knitted basket 14 and into the distal portion 18 of the elongated member 16.

The distal portion 18 of the elongated member 16 may have a different diameter and may be made of a different material than the rest of the elongated member 16. For ease of manufacture, it may be desirable that the distal portion 18 of the elongated member 16 have a similar diameter as the catheter 10. If the distal portion 18 is a different diameter than the rest of the elongated member 16, then the elongated member 16 may be embedded within the distal portion 18 to secure it in place.

The catheter wall 36 may comprise an inner layer which defines the lumen 38 of the catheter 10. The inner layer of the catheter wall may comprise a material such as PTFE. The wires 32 formed in a braid may be positioned on this inner layer. Additionally, a polymer may be applied to the inner layer and the wires 32 to form the outer surface of the catheter 10. The polymer may cover the first braided stage of the wires 32 entirely, filling in any gaps which may exist within the braid.

In FIGS. 4A-4G, eight possible embodiments of the knitted basket 14 are shown. These embodiments in no way comprise a complete list of possible embodiments, but only illustrate how various embodiments of the knitted basket 14 may be configured. All of the embodiments of the knitted basket 14 shown in FIGS. 4A-4G share some common elements. The knitted baskets 14 comprise a plurality of helical pairs 118 of wires 114 on the proximal and distal ends of the knitted basket 14. These helical pairs 118 comprise a continuous wrapping of the two component wires 114 around each other. Between the proximal and distal ends of the knitted basket 14, the helical pairs 118 of wires 114 separate into individual wires 116 which are integrated into the structure of the knitted basket 14. In the knitted basket 14, a individual wires 116 separate so that each wire 114 forms a series of interconnected windings 106. The interaction of these wires 114 form empty cells 110, 124, 130, 140, 148, 149 having a cell width 104, 122, 128, 138, 146, 152 when the knitted basket 14 is in its radially expanded position.

Each cell is comprised of four wires 114, a first pair 164 and a second pair 166, and four windings 106, a first winding 168, a second winding 170, and two side windings 172. The designation of each of the wire pairs 164, 166 and windings 106 are entirely dependent upon the individual cell 110, 124, 130, 140, 148, 149. A first pair 164 for one cell 110, 124, 130, 140, 148, 149 will form the second pair 166 for a different cell 110, 124, 130, 140, 148, 149. Similarly each side winding 172 will also be a first winding 168 and a second winding 170 depending on the cell 110, 124, 130, 140, 148, 149.

From the first winding 106, the first pair of wires 164 separate from the first winding 168 towards respective side windings 172 on either side of the cell 110, 124, 130, 140, 148, 149. The first pair of wires 164 proceed from the first winding 168 at a first angle 102, 120, 134, 136, 144 relative to the axis of the device's 22 movement within the intraluminal passage 28, a longitudinal axis. Similarly, the second pair of wires 164 converges toward the second winding 170 from respective side windings 172. The second pair of wires 166 converges on the second winding 170 at a second angle 103, 121, 135, 137, 144 relative to the axis of the device's 22 movement within the intraluminal passage 28, the longitudinal axis. These first and second angles 102, 103, 120, 121, 134, 135, 136, 138, 144, along with the radially expanded knitted basket 14 diameter 112 determines the cell 110, 124, 130, 140, 148, 149 shape and the radially expanded knitted basket length 108, 126, 132, 142, 150, 154, 156.

In determining the design of the knitted basket 14, several considerations may be taken into account. For example, the radial force that knitted basket 14 exerts as it expands is important to ensure that the wires 114 are forceful enough to pass through the thrombus 30. Additionally, the size of the cells 110, 124, 130, 140, 148, 149 formed by the knitted wires 114 in the knitted basket's 14 radially expanded position should be considered. If the cell width 104, 122, 128, 138, 146, 152 is too wide, the thrombus 30 may not be contained within the knitted basket 14 during retraction. However, if the wires 114 in the knitted basket 14 are spaced too closely together, creating very small cell width 104, 122, 128, 138, 146, 152, the thrombus 30 may fragment during the radial expansion of the knitted basket 14.

The length of the basket 14 in its expanded form may also be considered to ensure that the thrombus 30 can be contained within the knitted basked 14. The ratio of the lengths of the knitted basket 14 between its extended position over its radially expanded position may be another consideration. A high length ratio may allow for smaller cells 110, 124, 130, 140, 148, 149 to better capture the thrombus 30, however the knitted basket 14 may also require one or more support wires 24 to evenly expand. A small length ratio may allow for a shorter device 22 and easier radial expansion, but it may also create larger cells 110, 124, 130, 140, 148, 149 by which the thrombus 30 may escape during retraction.

The design of the knitted basket may also consider the effect of the knitted basket 14 while moving against the walls 26 of the intraluminal passage 28. During retraction of the knitted basket 14, the device 22 has a much larger cross-sectional profile as the knitted basket 14 is radially expanded. This may cause irritation or damage as the knitted basket 14 scrapes against the walls 26 of the intraluminal passage 28. To reduce the irritation to the walls 26 of the intraluminal passage 28, it may be desirable to utilize a basket 14 with wires 114 which, when the knitted basket 14 is radially expanded, form cells 110, 124, 130, 140, 148, 149 with wires 114 at small angles 102, 120, 134, 136, 144 relative to the axis of the device's 22 movement within the intraluminal passage 28, the longitudinal axis. Wires 114 on the knitted basket 14 which are oriented at high angles or perpendicular to the movement of the device 22 within the intraluminal passage 28 may cause more irritation to the walls 26 of the intraluminal passage 28.

Figure 4A:
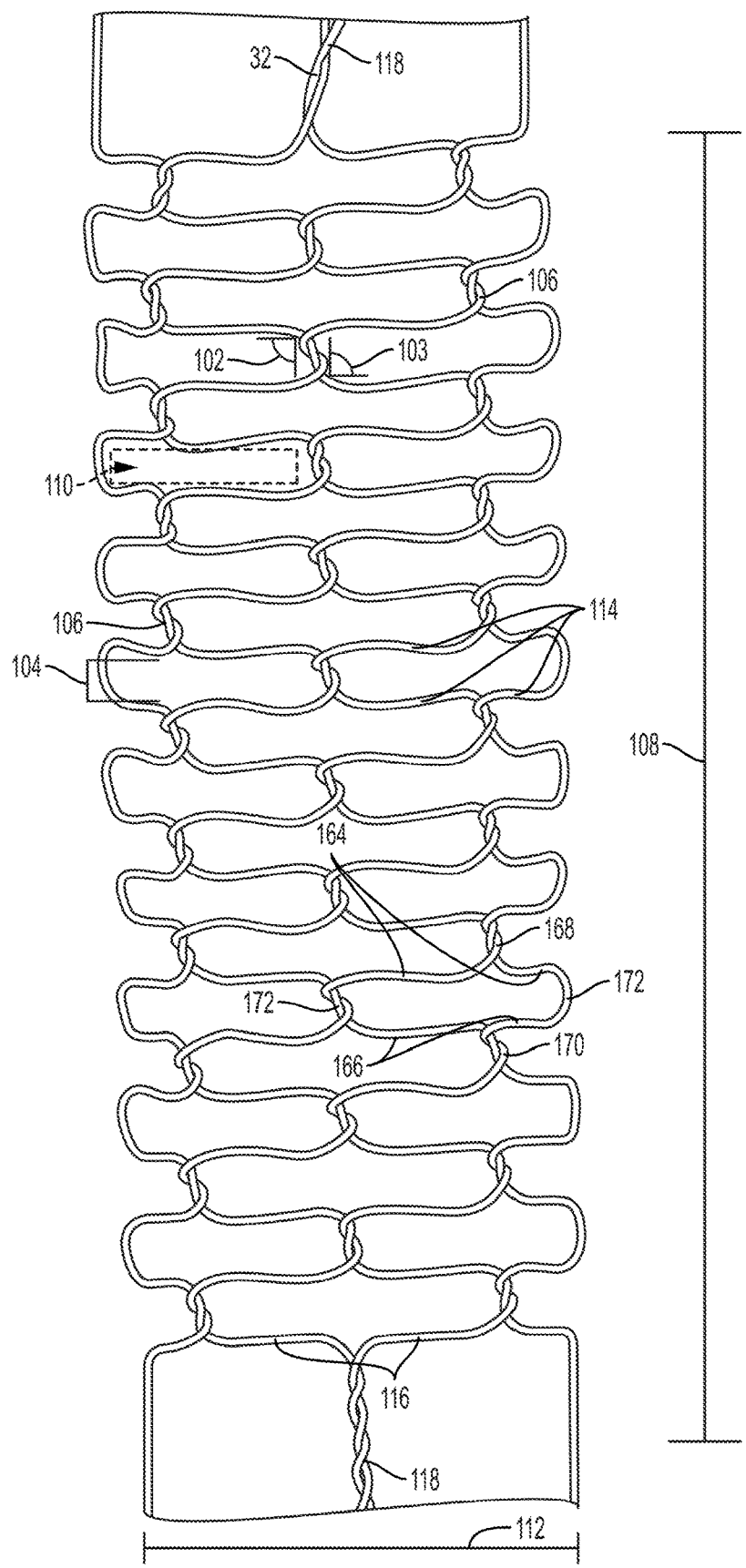
FIGS. 4A-4G are side plan views of knitted baskets, showing several possible configurations for the structure of a knitted basket.

FIG. 4A shows a knitted basket 14 wherein each cell 110 comprises a first pair of wires 164 and a second pair of wires 166 having a first and a second angle 102, 103 at or near 90 degrees. These angles angle 102, 103 results in cell 110 shapes which are roughly rectangular and have a very narrow cell width 104. When the knitted basket 14 is extended by the elongated member 16, the length of the knitted basket 14 proximal to the elongated member 16 may be up to 200% longer than the length 108 of the radially expanded knitted basket 14.

Figure 4B:
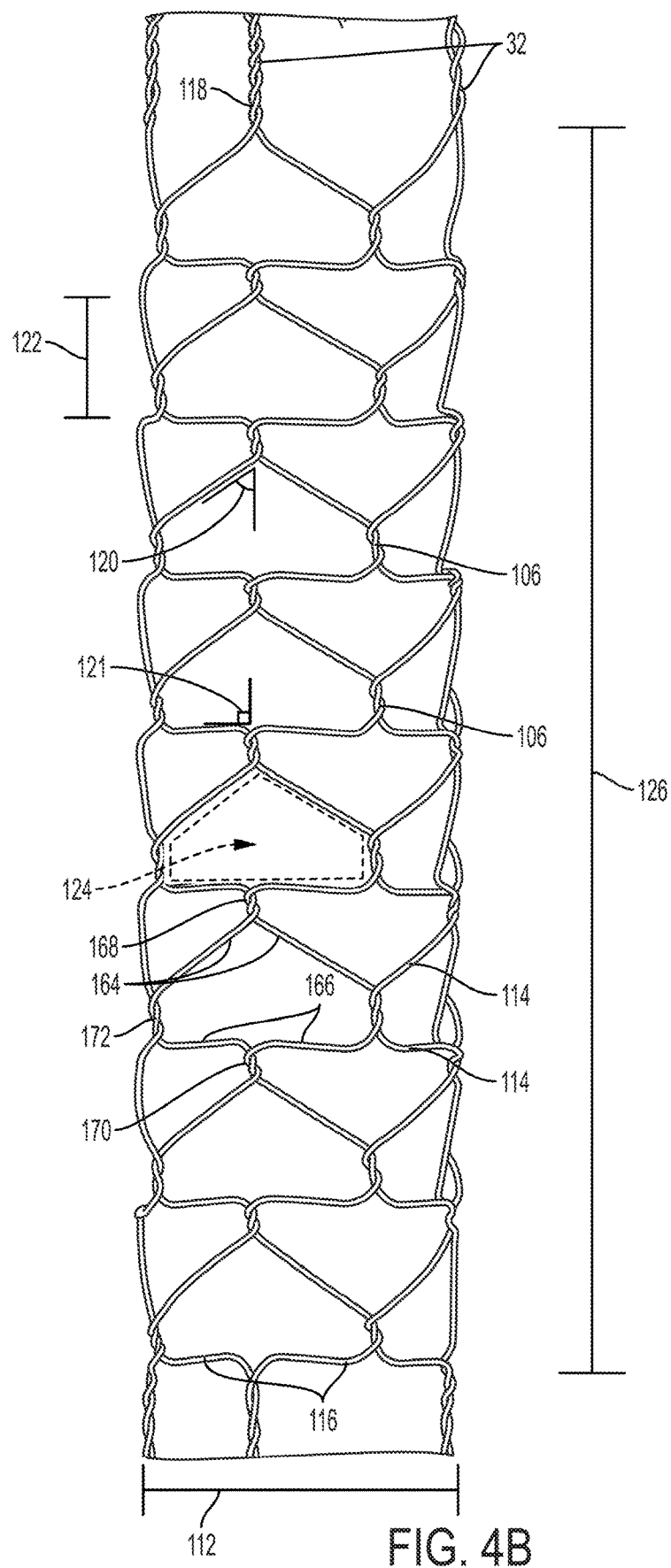

FIG. 4B shows a knitted basket 14 wherein each cell 124 comprises a first pair of wires 164 having a first angle 120 at or near 55 degrees, and a second pair of wires 166 having a second angle 121 at or near 90 degrees. These angles 120, 121 result in a cell 124 shape which is nearly triangular, with a wider cell width 122 than the cell 110 shape shown in FIG. 4A. When the knitted basket 14 is extended by the elongated member 16, the length of the knitted basket 14 proximal to the elongated member 16 may be up to 90% longer than the length 126 of the radially expanded knitted basket 14.

Figure 4C:
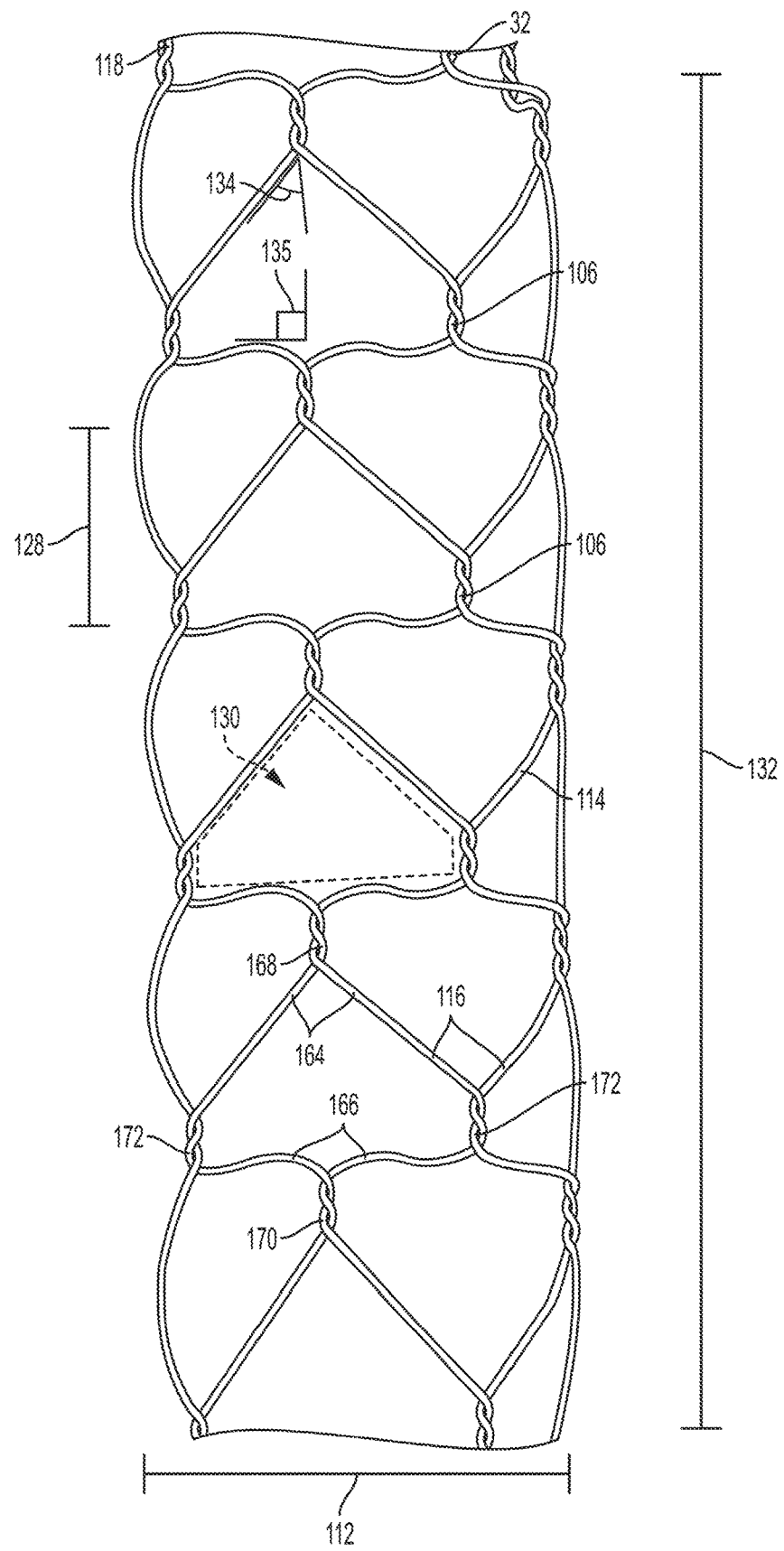

FIG. 4C shows a knitted basket 14 wherein each cell 130 comprises a first pair of wires 164 having a first angle 134 at or near 40 degrees, and a second pair of wires 166 having a second angle 135 at or near 90 degrees. These angles 134, 135 result in a cell 130 shape which is nearly triangular, with a wider cell width 128 than the cell 124 shape shown in FIG. 4B. When the knitted basket 14 is extended by the elongated member 16, the length of the knitted basket 14 proximal to the elongated member 16 may be up to 50% longer than the length 132 of the radially expanded knitted basket 14.

Figure 4D:
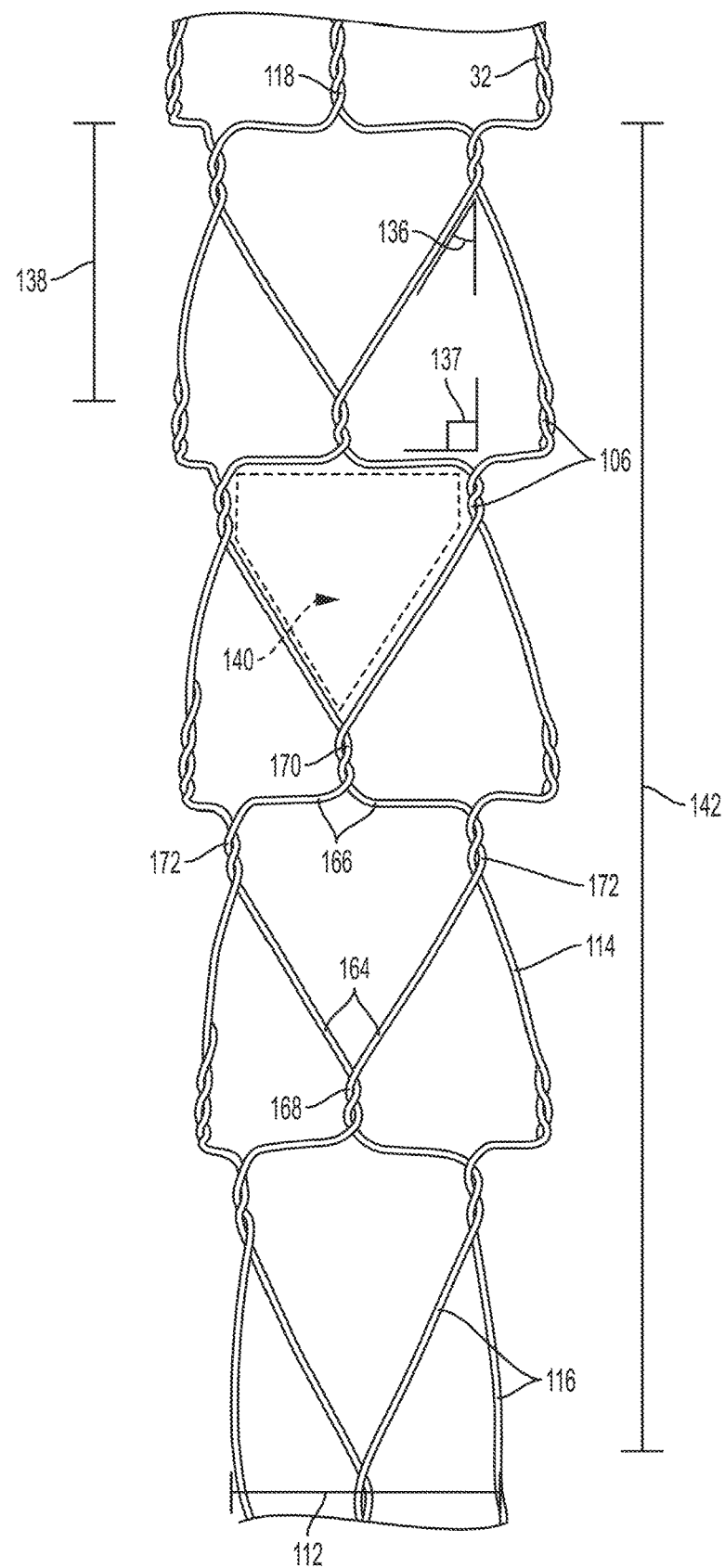

FIG. 4D shows a knitted basket 14 wherein each cell 140 comprises a first pair of wires 164 having a first angle 136 at or near 35 degrees, and a second pair of wires 166 having a second angle 137 at or near 90 degrees. These angles 136, 137 result in a cell 140 shape which is nearly triangular, with a wider cell width 138 than the cell 130 shape shown in FIG. 4C. When the knitted basket 14 is extended by the elongated member 16, the length of the knitted basket 14 proximal to the elongated member 16 may be up to 30% longer than the length 142 of the radially expanded knitted basket 14.

Figure 4E:
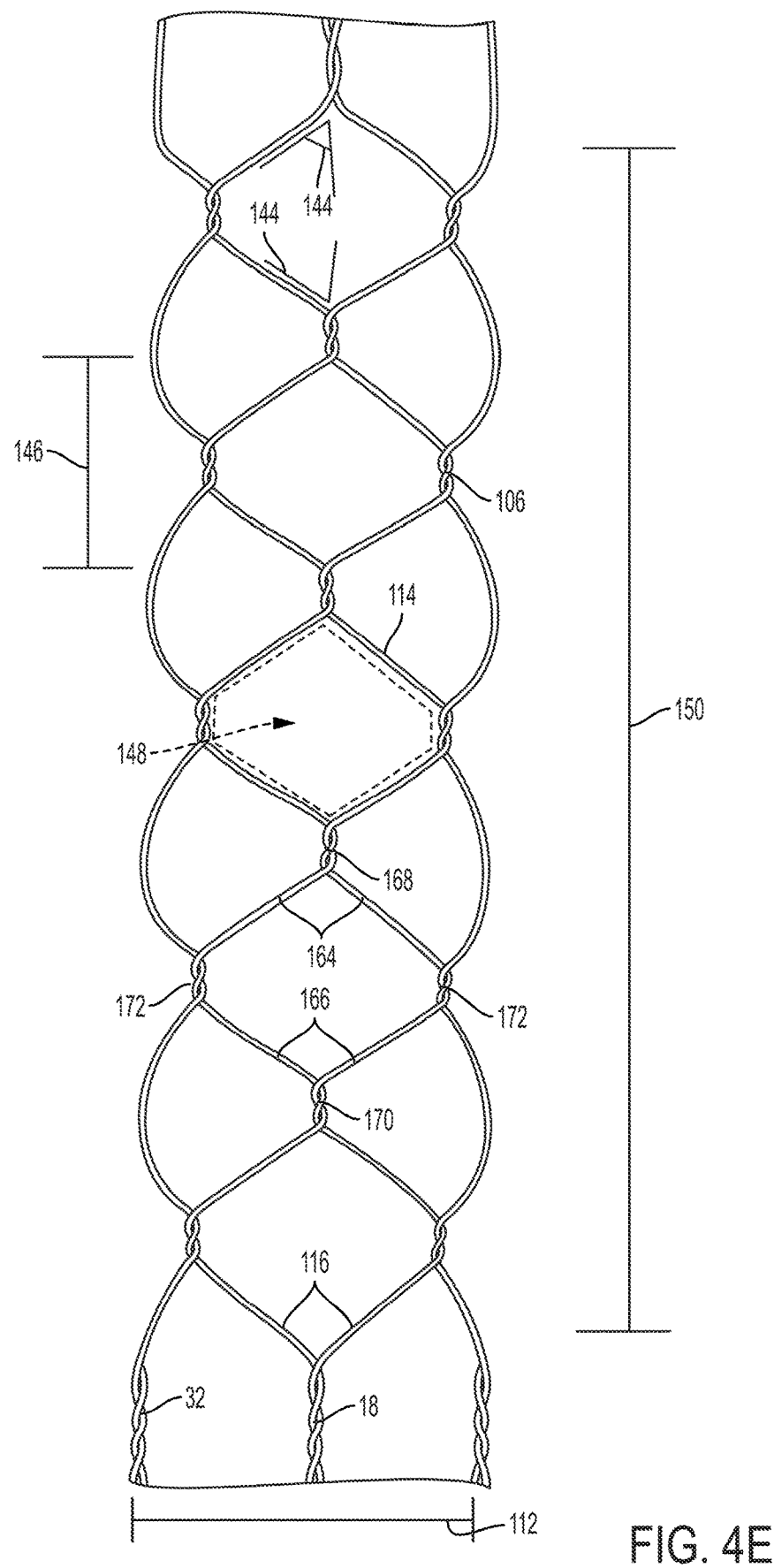

FIG. 4E shows a knitted basket 14 wherein each cell 148 comprises a first pair of wires 164 and a second pair of wires 166 having identical angles 144 at or near 55 degrees. This results in a cell 148 shape which is nearly diamond-shaped, with a wider cell width 122 than the cell 124 shape shown in FIG. 4B but a shorter cell width 122 than the cell 130 shown in FIG. 4C. When the knitted basket 14 is extended by the elongated member 16, the length of the knitted basket 14 proximal to the elongated member 16 may be up to 90% longer than the length 150 of the radially expanded knitted basket 14.

Figure 4F:
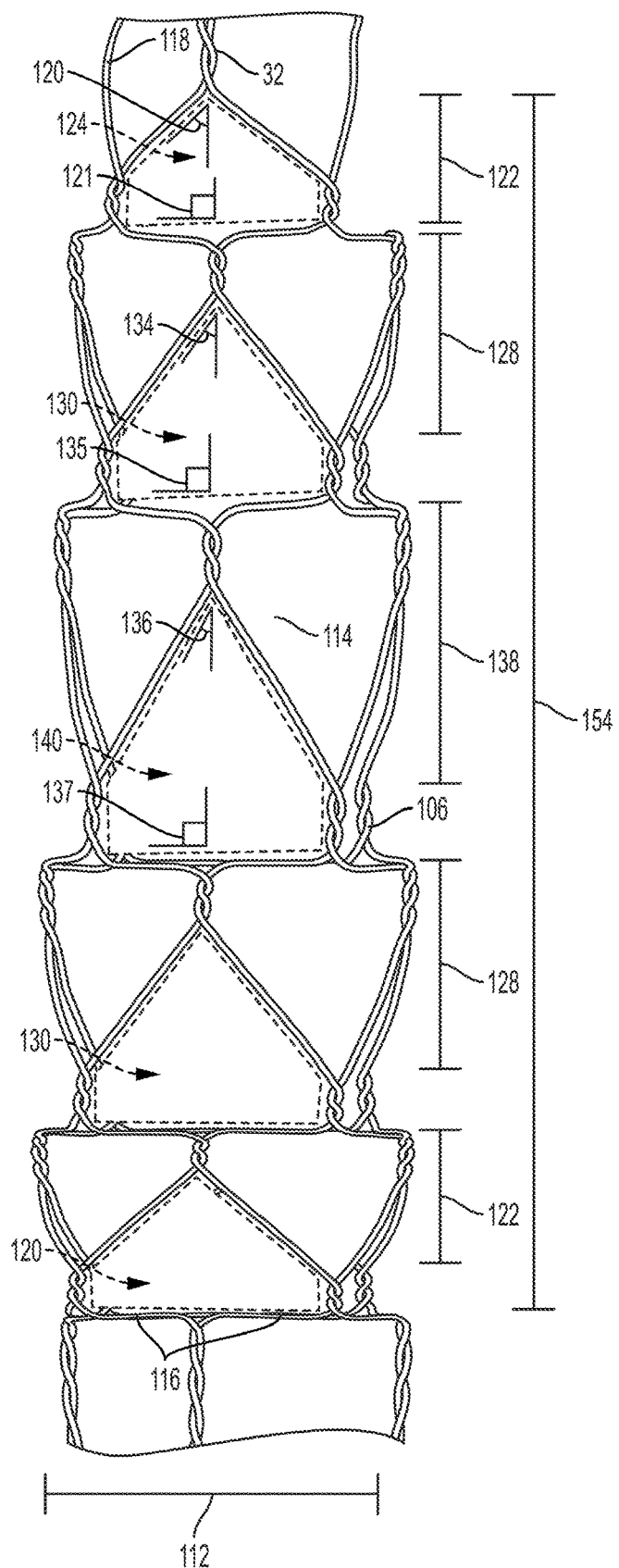

FIG. 4F shows a knitted basket 14 comprising wires 114 at varying angles 120, 121, 134, 135, 136, 137 to create cell 124, 130, 140 shapes which having an increasing cell width 122, 128, 138 as the cells approach the center of the knitted basket 14. In the embodiment shown, the knitted basket 14 has one set of cells 124 similar to those shown in FIG. 4B on both the proximal and distal end of the knitted basket 14. Closer to the center from that layer, is an additional layer of cells 130 similar to those shown in FIG. 4C, which are wider than the cells 124 shown in FIG. 4B. In the center of the knitted basket 14 is a single layer of cells 140 similar to those found in FIG. 4D, which has the widest cell width 138. When the knitted basket 14 is extended by the elongated member 16, the length of the knitted basket 14 proximal to the elongated member 16 may be up to 60% longer than the length 154 of the radially expanded knitted basket 14.

Figure 4G:
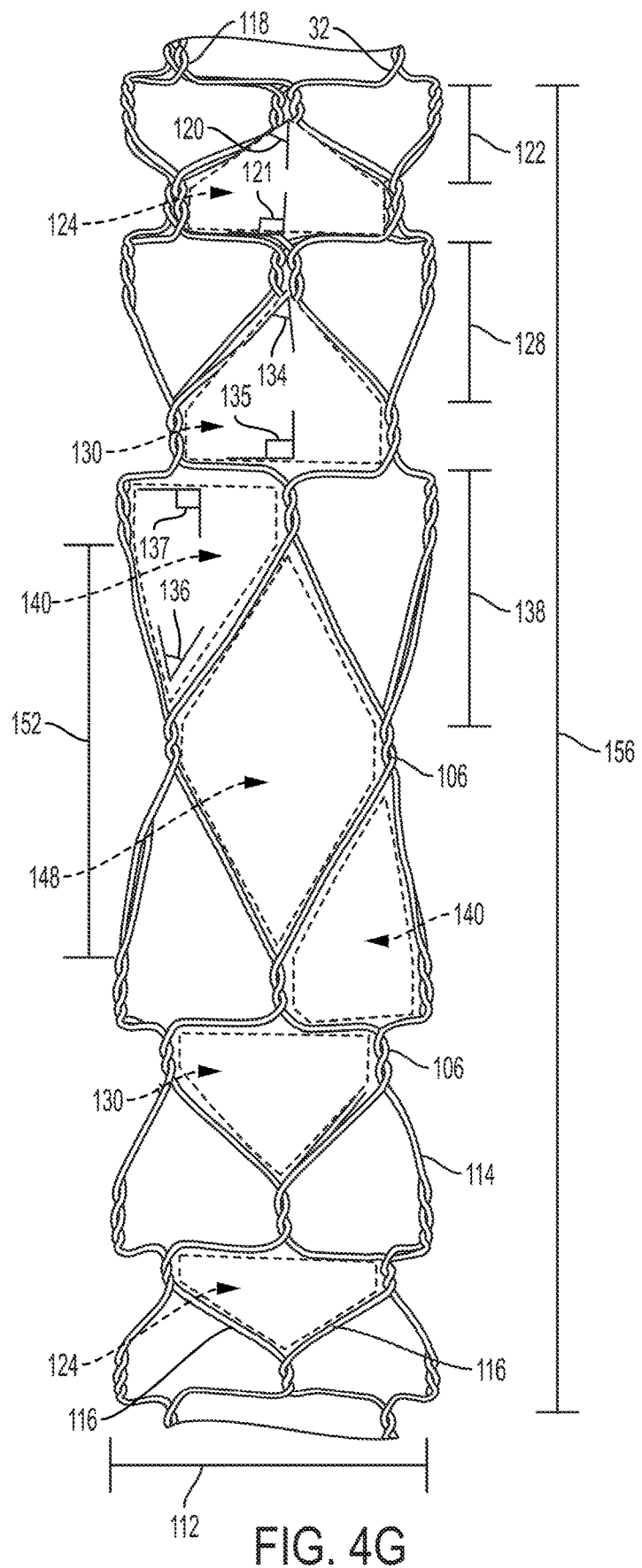

FIG. 4G shows a knitted basket similar to that shown in FIG. 4F, wherein the cell width 122, 128, 138, 152 increases closer to the center of knitted basket 14. However, unlike FIG. 4F, the cells 124, 130, 140 are arranged in such a way to create large diamond cells 149 at the center of the knitted basket 14, each having a very large cell width 152, wider than any of the other cell widths 122, 128, 152. When the knitted basket 14 is extended by the elongated member 16, the length of the knitted basket 14 proximal to the elongated member 16 may be up to 40% longer than the length 150 of the radially expanded knitted basket 14.

Figure 5A:
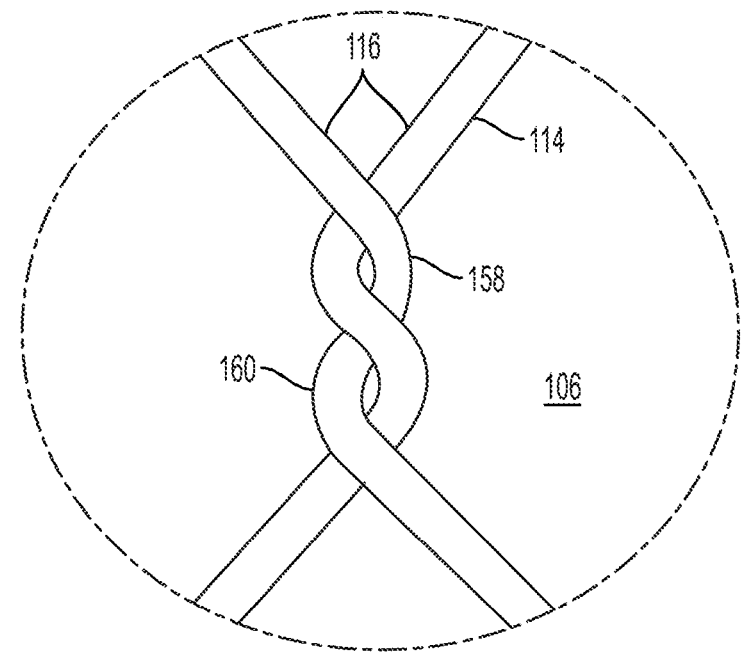
FIG. 5A is a close-in, plan view of a knitted basket, showing a winding between two wires.

FIG. 5A shows an example of a winding 106 between wires 114 in the knitted basket 14. The configuration shown in FIG. 5 is a double-twist winding 106, wherein the wires 114 are twisted (158, 160) around each other twice, each wire 114 being twisted substantially 360 degrees. Each twist 158 alters the direction of the wires 114 substantially 180 degrees. The first twist 158 alters the direction of the wire 114 and reflects its direction, while the second twist 160 maintains each wire 114 along its original path prior to the winding 106. Although a double-twist winding 106 is shown here, other number of windings 106 may be appropriate for various circumstances. Knitted baskets 14 consisting of fewer twists in their windings 106 will use less wire 114 length and may be more flexible. However, knitted baskets 14 with more twists in their windings 106 may be more structurally rigid, holding their shape more consistently in the extended and compressed forms. A high number of twists in each winding may, however, affect the shape of the cell, 110, 124, 130, 140, 148, 149, decreasing the knitted basket's 14 ability effectively compress and expand. As a result, it may be desirable to limit windings to 5 or fewer twists.

Furthermore, an even number of twists in each winding 106 will result in individual wires 114 being twisted by an angle of substantially 360 degrees, 720 degrees, or some other similar angle. Such a winding 106, when repeated on the entire knitted basket 114, will result in the wires 114 spiraling around the circumference of the knitted basket 14. This configuration may be desirable to give the knitted basket 14 additional stability and to prevent collapsing or kinking during radial expansion. Alternatively, an odd number of twists in each winding 106 will result in individual wires 114 being twisted by an angle of substantially 180 degrees, 540 degrees, or some similar angle. Such a winding 106, when repeated on the entire knitted basket 14, will result in the wires 114 reconnecting with the same individual wire 114 every other winding 106 and remaining in a circumferentially stable position along the length of the knitted basket 14. This configuration may however be less stable and may cause kinking or collapsing of the knitted basket 14 during radial expansion, depending on the forces exerted on the wires 114 during radial expansion.

Figure 5B:
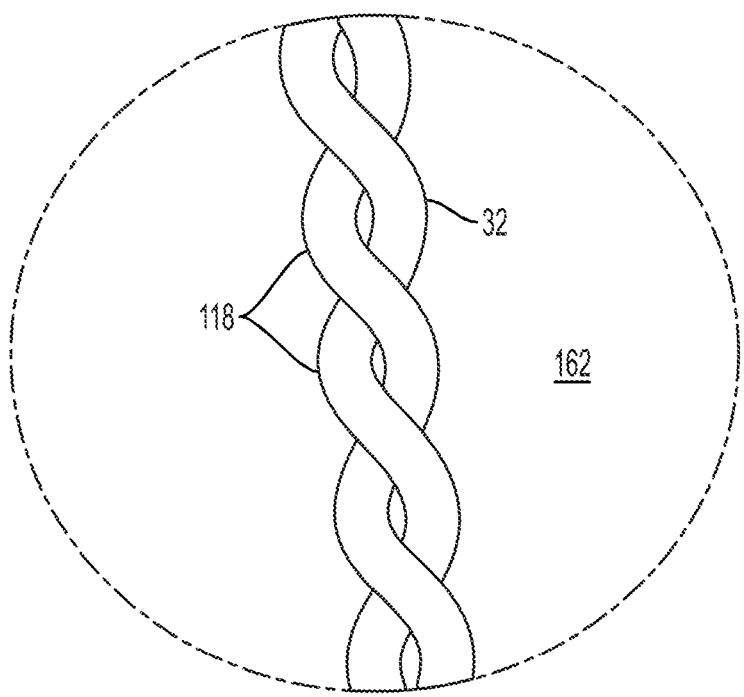
FIG. 5B is a close-in, plan view of a twisted pair of wires in a continuous twist.

Referring to FIG. 5B, an example of a helical pair 118 of wires 32 is shown in a continuous twist 162. In contrast to the winding 106 shown in FIG. 5A, the helical pair 118 of wires 32 are arranged in a continuous braid or twist typically comprising at least 5 consecutive twists, so that each of the helical pair 118 of wires 32 is continuously adjacent to each other. The braiding or twisting may, however, extend the entire length of the catheter 10. The arrangement of the helical pairs 118 is advantageous since it allows the helical pairs to take up a small amount of space while spiraling within the wall 26 of the catheter 10. After passing through the distal end 34 of the catheter 10, however, the helical pair 118 can be separated to be integrated into the knitted basket 14. It may be desirable that the helical pairs 118 are twisted in the same direction at the windings 106 in the knitted basket 14 to increase the stability of the knitted basket 14 and to prevent collapsing or kinking during radial expansion. For example, if the helical pairs 118 are twisted or braided together in a clockwise fashion, then it may be desirable to twist the windings 106 in in the knitted basket 14 in the same clockwise direction.

Figure 6A:
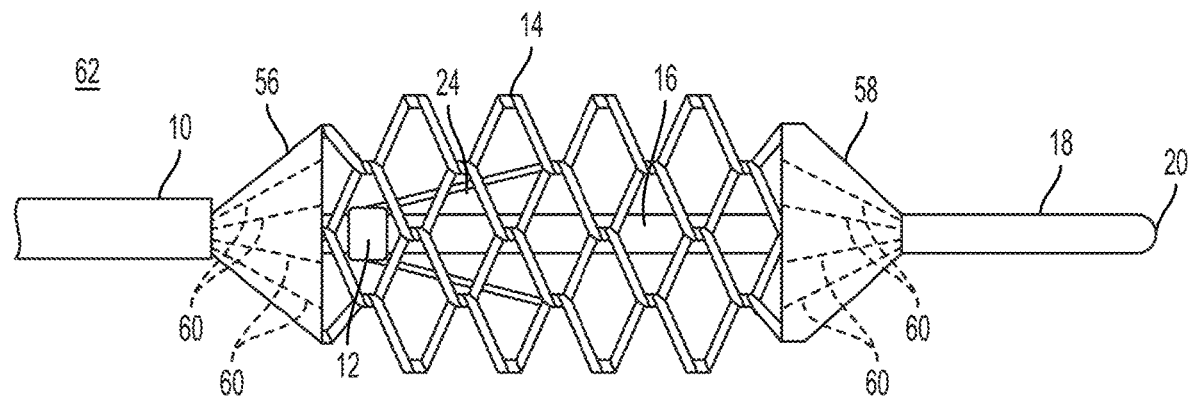
FIG. 6A is a side plan view of a clot retrieval device, showing an outer catheter, an inner elongated member, and a knitted basket which includes proximal and distal coverings.
Figure 6B:
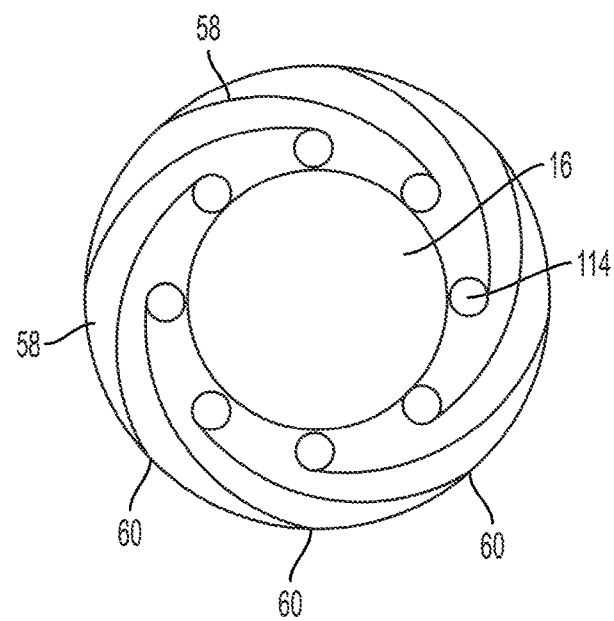
FIG. 6B is a cross-sectional axial view of a clot retrieval device, showing an inner elongated member, a plurality of wires and a folded covering.

Referring to FIGS. 6A and 6B, another embodiment of the clot retrieval device 62 is shown with proximal and distal coverings 56, 58 on the proximal and distal ends of the knitted basket 14. The coverings may be made of a thin flexible material which is compressible. The coverings 56, 58 are coupled to the wires 114 of the knitted basket 14. The proximal covering's 56 proximal side may also be coupled to the catheter's 10 distal end 34, while distal covering's 58 distal side may also be coupled to the distal portion 18 of the elongated member 16. When the elongated member 16 is in the extended position, the proximal and distal coverings 56, 58 compress so that the entire cover 56, 58 is adjacent to the outer surface of the elongated member 16. When the elongated member 16 is in the compressed position, the proximal and distal coverings 56, 58 expand radially along with the knitted basket 14. The coverings 56, 58 may be configured on the knitted basket 14 so that the portions of the coverings further from the center of the knitted basket 14 expand less than the portions closer to the center of the knitted basket. If the ends of the coverings 56, 58 are coupled to the catheter's 10 distal end 34 or the elongated member's 16 distal portion 18, those ends of the coverings 56, 58 may not expand at all. While expanded, the coverings 56, 58 are effective in controlling the proximal and distal motion of the thrombus 30 which is contained within the knitted basket 14.

To ensure that the cross-sectional profile of the clot retrieval device 62 is as small as possible, it may be desirable to include pre-set folds into the proximal and distal coverings 56, 58 by defining fold lines 60 on the surface of the coverings 56, 58. It may be desirable to place these fold lines 60 off-center between the wires 114 of the knitted basket 14, so that when the elongated member 16 is in the extended position, the proximal and distal coverings 56, 58 fold at the fold lines in a spiral pattern, as shown in FIG. 6B.

Figure 7:
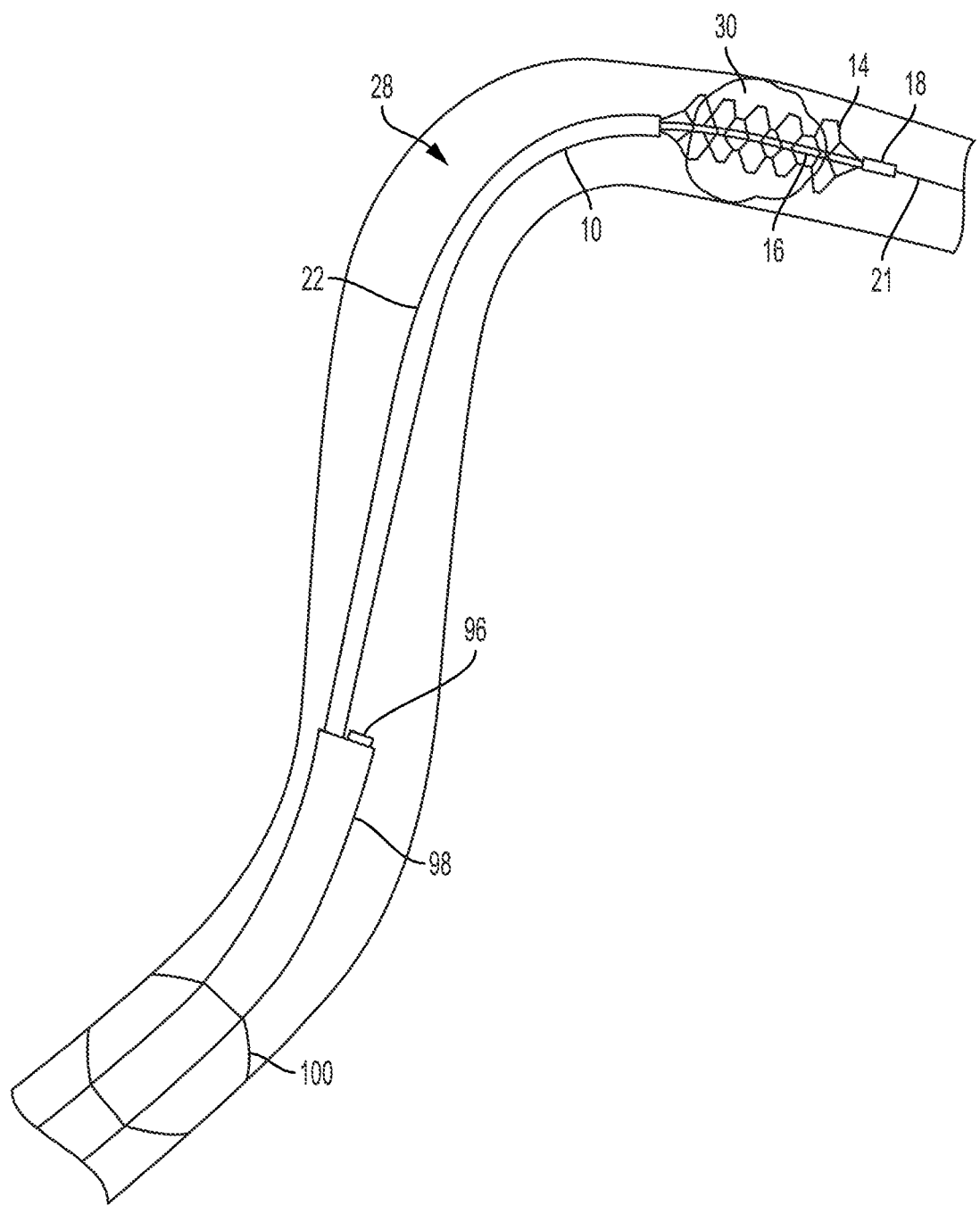
FIG. 7 is a side plan view of a clot retrieval system, showing an intraluminal passage, a thrombus, a clot retrieval device, and an inflatable aspirating sheath.

Referring to FIG. 7, a clot retrieval system is shown which includes a wire guide 21, a knitted basket 14 coupled to a catheter 10 and an elongated member 16, an aspiration catheter 96, and a sheath 98 which includes an inflatable member 100.

For narrow or tortuous intraluminal passages 28, it may be desirable to initially advance a wire guide 21 to the thrombus 30 because of a wire guide's smaller cross-sectional profile and steerability. As shown in FIG. 7, the clot retrieval device 22, may configured to be advanced over a wire guide 21. To accommodate a wire guide 21, the elongated member 16 may comprise a lumen. The wire guide 21 passes through this lumen so that the clot retrieval device 22 may be advanced to the thrombus 30.

Fragmentation of the thrombus 30 during retrieval may be a risk in some operations. To prevent fragmentation from causing complications to the patient, it may be desirable to include an additional sheath 98 with the clot retrieval device 22. This sheath 98 may be advanced over the clot retrieval device 22, or alongside the device. If the sheath 98 is to be advanced over the clot retrieval device 22, the sheath 98 will have a first lumen which the device 22 may pass through.

The sheath 98 may also have a second lumen to accommodate an aspiration catheter 96, which may use suction to collect fragmented portions of the thrombus 30 and prevent their circulation throughout the patient's body. Alternatively, the aspiration catheter 96 may also be brought in proximity of the knitted basket 14 after the capture of the thrombus 30 to safely remove the thrombus 30. In this way, it would not be necessary to maintain the elongated member 16 in its extended position during the retraction of the clot retrieval device 22.

The sheath 98 may also include an inflatable member 100 located proximally from the knitted basket 14. This inflatable member 100 may be inflated to block the flow of blood within the intraluminal passage 28, allowing safe retrieval of the thrombus 30 and any fragments which may result from its capture within the knitted basket 14. The inflatable member 100 may be inflated by a third lumen within the sheath 98.

Figure 8:
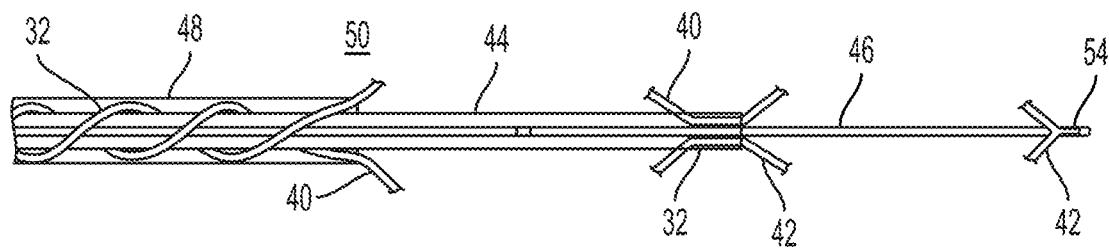
FIG. 8 is a partial cross-sectional view of a clot retrieval device, showing a plurality of knitted baskets, an outer catheter, an inner catheter, and an elongated member.

In some operations, it may be desirable to have multiple knitted baskets 40, 42 to retrieve more than one thrombus 30. Referring to FIG. 8, yet another embodiment of the clot retrieval device 50 is shown having a plurality of knitted baskets 40, 42. For simplicity, the bodies of the baskets 40, 42 are omitted, however the design of the baskets 40, 42 may be similar to any of the designs discussed above. In the embodiment of FIG. 8, an first outer catheter 48 is shown having a second inner catheter 44 disposed within a lumen of the first outer catheter 48. Furthermore, an elongated member 46 is disposed within a lumen of the second inner catheter 44. The first outer catheter 48 and the second inner catheter 44 are movable between a longitudinally extended position, and a longitudinally compressed position, which controls the radial expansion of the first basket 40. Similarly, the second inner catheter 44 and the elongated member 46, are separately movable between a longitudinally extended position and a longitudinally compressed position, which controls the radial expansion of the second basket 42. In this way, each knitted basket 40, 46 may be separately radially expanded to capture different thrombi 30 or different portions of a larger thrombus 30.

The knitted baskets 40, 42, shown in FIG. 8 comprise a single set of wires 114 which run at least from the distal end of the first outer catheter 48 to the distal portion 54 of the elongated member 46. Within the first outer catheter, the wires 114 are arranged in helical pairs 118, which spiral within the walls of the first outer catheter 48. Distal from the distal end of the first outer catheter 48, the helical pairs 118 separate to be integrated into the first knitted basket 40. Distal from the first knitted basket 40, helical pairs 118 are reformed and are embedded within the walls of the distal end of the second inner catheter 44. Distal from the distal end of the second inner catheter 44, the helical pairs 118 separate to be integrated into the second knitted basket 42. At the distal portion 54 of the elongated member 46, the wires 114 form helical pairs 118 and are embedded within the elongated member 46. Alternatively, the first and second baskets 40, 42 may comprise two unconnected sets of knitted wires 114, however, this may increase the size and cost of manufacturing the device 50.

When using the multi-basket device 50, it may be desirable to pass through or around the first proximal thrombus with the elongated member 46 and the second inner catheter 44, positioning at least a portion of the first proximal thrombus to overlap with the first basket 40. The first outer catheter 48 and the second inner catheter 44 may be moved to the compressed position to radially expand the first basket 40 and capture the first proximal thrombus within. The device may then be advanced further so that the elongated member 46 passes through or around a second distal thrombus, positioning at least a portion of the second distal thrombus to overlap with the second basket 42. The second inner catheter 44 and the elongated member 46 may then be moved to the compressed position to radially expand the second basket 42 and capture the second distal thrombus within. The device 50 may then be retracted to clear the intraluminal passage 28.

Alternatively, if the thrombus 30 is too large to be retrieved with a single knitted basket 14, the multi-basket device 50 may be used so that a proximal portion of the thrombus 30 may be captured within the first basket 40, and the distal portion of the thrombus 30 may be captured within the second basket 42. Similar designs could be used providing additional baskets to retrieve a larger thrombus 30 within a narrow intraluminal passage 28.

Figure 9A:
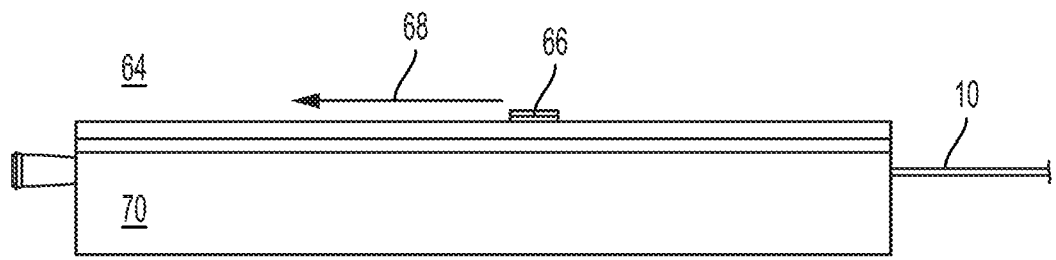
FIG. 9A is a side plan view of an actuator for a clot retrieval device, showing the movement of a button in relation to a casing.
Figure 9B:
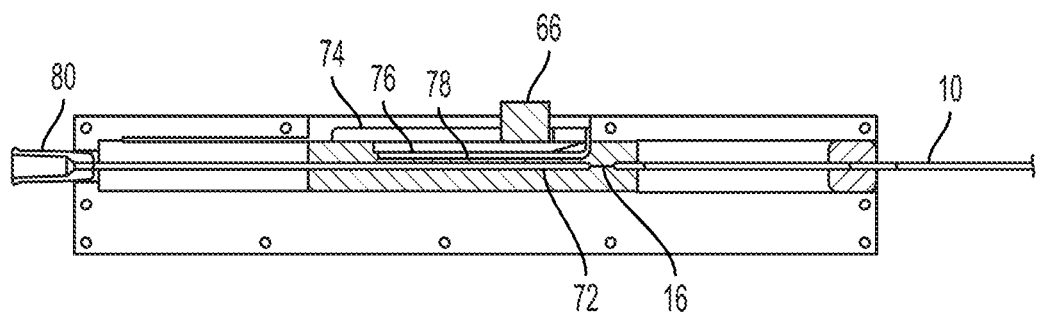
FIG. 9B is a cross-sectional view of an actuator for a clot retrieval device, showing a button within a slot, and a sledge.

Referring to FIGS. 9A and 9B, an embodiment of an actuator 64 for controlling a clot retrieval device 22 is shown. The actuator 64 comprises a casing 70 which encircles the elongated member 16 with a button 66 protruding from the casing's outer surface. This button 66 may be moved proximally 68 to move the inner elongated member 16 from the extended position to the compressed position, causing the knitted basket 14 to radially expand. In the embodiment shown, the button 66 is coupled to a sledge 76 which is configured to move distally within a slot 74. The sledge 76 is coupled to a stopping plate 78 which is configured to limit the proximal motion of the button. The stopping plate 78, button 66, or sledge 76 may be coupled to a grip 72 which is in turn coupled to the elongated member 16. Relative movement between the catheter 10 and the elongated member 16 is achieved by embedding the proximal end of the catheter 10 within the casing 70 of the handle 64, which ensures that the catheter's 10 position is unchanged when the button is moved proximally or distally. Additionally, an introducer 80 may be included on the proximal end of the handle 70 if a wire guide 21 is to be utilized. The wire guide 21 is placed within a lumen of the introducer 80, which is configured to enter into a lumen of the elongated member 16.

The radially expansion of the knitted basket 14 may be finely controlled by movement of the button 66 proximally or distally. If the knitted basket 14 is being expanded within a very narrow intraluminal passage 28, there may not be sufficient space to fully expand the knitted basket 14. The operator may track the expansion and placement of the basket 14 through a method such as fluoroscopy and use the button 66 to adjust the expansion of the basket 14 to capture the thrombus 30 without straining the walls 26 of the intraluminal passage. Once captured, the thrombus 30 may be partially retracted to a position within the intraluminal passage 28 where the basket 14 may be fully radially expanded.

During manufacture of the device 22, it may be desirable to heat set the knitted basket 14 in the radially expanded or the radially unexpanded position. In this way, the knitted basket 14 will exert a force to return to that position. If the basket 14 is heat set in the radially expanded position, there may be a slight constant proximal force on the button 66 which the operator would have to overcome. Similarly, if the basket 14 is heat set in the radially unexpanded position, the knitted basket 14 may exert a slight distal force on the button 66. In such a design, once deployed, the operator would have to exert a proximal force to maintain the radial expansion of the knitted basket 14 and could release the thrombus 30 by releasing the button 66.

Referring to FIGS. 10A-10D, another embodiment of a handle 82 for operating a clot retrieval device 22 is shown. The handle 82 shown comprises an inner slidable member 90 and an outer sleeve 84. The outer sleeve 84 encircles the elongated member 16 and has a plurality of inwardly projecting members 92 arranged in a straight line along the longitudinal axis of the device. The inner slidable member 90 extends from the proximal end of the outer sleeve 84 and comprises a cavity 86 at least large enough to accommodate the inwardly projecting members 92 of the outer sleeve 84. The cavity 86 is arranged on the outer surface of the slidable member 90 and is defined by a region of increased separation between the outer surface of the slidable member 90 and the inner surface of the outer sleeve 84. The inner slidable member 90 also comprises at least one engaging member 94 projecting into a portion of the cavity 86, and at least one control surface 88 on the distal portion of the inner slidable member 90.

Figure 10A:
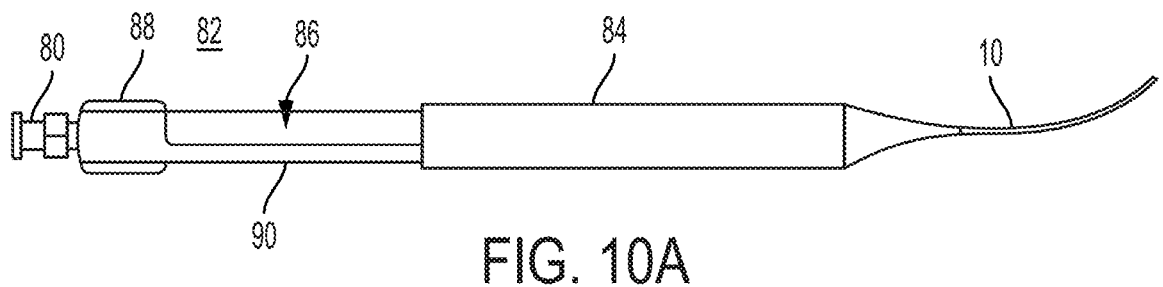
FIGS. 10A-10D are partial cross-sectional views of an actuator for a clot retrieval device, showing the method of operation between an outer slidable member and an inner slidable member.
Figure 10B:
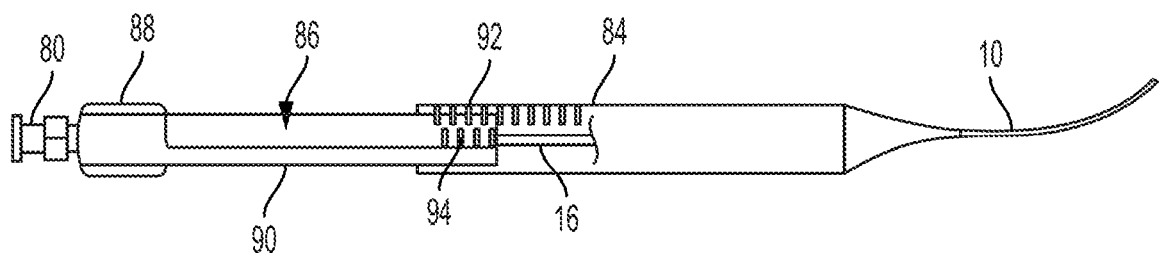
Figure 10C:
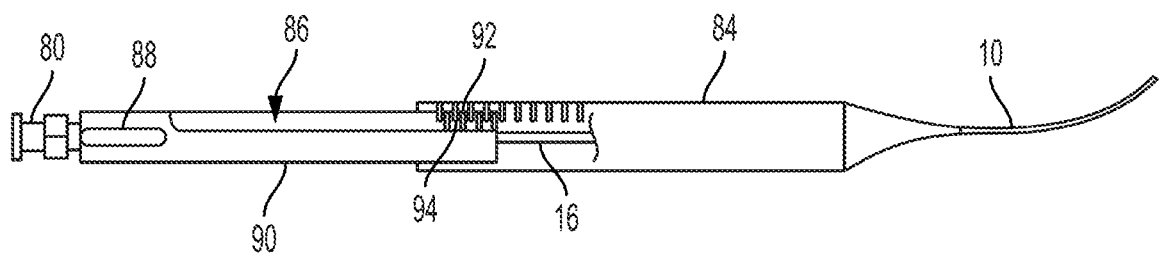

The outer sleeve 84 is coupled to the catheter 10 of the clot retrieval device 22. The inner slidable member 90 is coupled to the elongated member 16, so that moving the inner slidable member 90 relative to the outer sleeve 84, moves the elongated member 16 relative to the catheter 10 between the extended position and the compressed position. FIGS. 10A-10C show the handle 82 when the elongated member 16 is in the compressed position. To adjust the position of the elongated member 16 to the extended position, the slidable member is advanced distally.

Figure 10D:
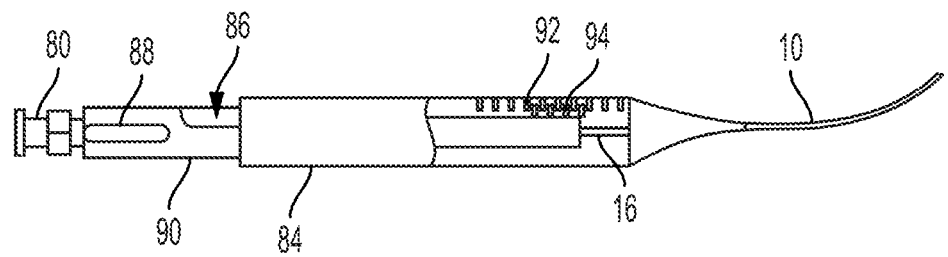

The handle 82 allows the operator to finely adjust and lock the position of the elongated member 16 and the radial expansion of the knitted basket 14. The handle is in the locked position in FIG. 10C, with the elongated member in the compressed position. In this position, the inwardly projecting members 92 of the outer sleeve 84 overlap with the engaging members 94 within the cavity 86 of the inner slidable member 90. To unlock the handle 82, the inner slidable member 90 may be rotated relative to the outer sleeve 84 so that the inwardly projecting members 92 no longer overlap with the engaging member 94 within the cavity 86. In this position, the inner slidable member 90 may be advanced as need by the operator to change the position of the elongated member 16 and the radial expansion of the knitted basket 14, as shown in FIG. 10D. Once the position is reached, the handle 82 may be locked by rotating the inner slidable member 90 relative to the outer sleeve 84 so that the inwardly projecting members 92 again overlap with the engaging members 94 within the cavity 86.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to embrace them.

We claim:

1. A method of retrieving an obstruction within an intraluminal passage, comprising:
   inserting a retrieval device into an intraluminal passage, the retrieval device comprising an outer catheter, an elongated member extending through a lumen of the outer catheter, and a basket having a proximal end coupled to the outer catheter and a distal end coupled to the elongated member, wherein the basket comprises a plurality of cells defined by interconnected windings of a plurality of wires, the windings comprising one of the plurality of wires twisted about another of the plurality of wires;
   positioning the basket alongside the obstruction while the basket is compressed against the elongated member; and
   radially expanding the basket to capture a portion of the obstruction within the basket, wherein the basket is radially expanded by relative movement between the outer catheter and the elongated member.

2. The method of claim 1, wherein when radially expanding the basket, at least one of the plurality of wires passes through the obstruction.

3. The method of claim 1, wherein when radially expanding the basket, the portion of the obstruction passes through one of the plurality of cells into the basket.

4. The method of claim 3, wherein a width of at least one of the plurality of cells decreases as the basket expands.

5. The method of claim 1, further comprising locking the position of the elongated member with respect to the outer catheter such that the basket is maintained compressed against the elongated member.

6. The method of claim 1, further comprising locking the position of the elongated member with respect to the outer catheter such that the radial expansion of the basket is maintained.

7. The method of claim 1, further comprising moving the basket to a position proximate an aspiration catheter after capturing the portion of the obstruction.

8. The method of claim 1, wherein the basket is knitted.

9. The method of claim 1, wherein each winding is a double-twist winding.

10. The method of claim 1, wherein the number of twists in each winding is even.

11. The method of claim 1, wherein the number of twists in each winding is odd.

12. The method of claim 1, wherein a distal portion of the elongated member comprises an atraumatic tip having a rounded end.

13. The method of claim 1, wherein the elongated member comprises a lumen, and the method comprises initially advancing a wire guide to a location of the obstruction and advancing the retrieval device over the wire guide.

14. The method of claim 1, wherein each cell of the basket comprises four wires.

15. The method of claim 1, wherein each cell comprises four windings.

16. The method of claim 1, wherein a shape of each cell is triangular or diamond-shaped.

17. The method of claim 1, wherein each of the plurality of wires spirals around a circumference of the basket.

* * * * *